United States Patent [19]
Apelian et al.

[11] Patent Number: 6,153,223
[45] Date of Patent: Nov. 28, 2000

[54] STABILIZED PHARMACEUTICAL COMPOSITIONS

[75] Inventors: Vahe Henry Apelian, Loveland; Nilesh H. Parikh, West Chester, both of Ohio; Raman Iyer, Glen Allen, Va.

[73] Assignee: Watson Pharmaceuticals, Inc., Corona, Calif.

[21] Appl. No.: 09/092,388

[22] Filed: Jun. 5, 1998

[51] Int. Cl.$^7$ .................................. A61K 9/14; A61K 9/20
[52] U.S. Cl. ..................... 424/489; 424/464; 424/465; 514/777; 514/778; 514/781; 514/970; 514/973
[58] Field of Search ...................................... 424/464, 465, 424/468, 469, 489, 452; 514/970

[56] References Cited

U.S. PATENT DOCUMENTS

| | | | |
|---|---|---|---|
| Re. 33,994 | 7/1992 | Baker et al. | 424/464 |
| 3,819,706 | 6/1974 | Mehta | 260/570.5 |
| 3,885,046 | 5/1975 | Mehta | 424/330 |
| 4,434,152 | 2/1984 | Horvath et al. | 424/19 |
| 4,591,592 | 5/1986 | Chowhan | 514/301 |
| 4,743,450 | 5/1988 | Harris et al. | 424/440 |
| 5,098,715 | 3/1992 | McCabe et al. | 424/479 |
| 5,225,204 | 7/1993 | Chen et al. | 424/484 |
| 5,358,970 | 10/1994 | Ruff et al. | 514/649 |
| 5,427,798 | 6/1995 | Ludwig et al. | 424/464 |
| 5,541,231 | 7/1996 | Ruff et al. | 514/649 |
| 5,560,924 | 10/1996 | Wunderlich et al. | 424/451 |
| 5,562,921 | 10/1996 | Sherman | 424/465 |
| 5,573,780 | 11/1996 | Sherman | 424/464 |
| 5,731,000 | 3/1998 | Ruff et al. | 424/451 |
| 5,763,493 | 6/1998 | Ruff et al. | 514/617 |
| 5,968,553 | 10/1999 | Maitra et al. | 424/474 |

FOREIGN PATENT DOCUMENTS

| | | |
|---|---|---|
| 90101211 | 6/1990 | European Pat. Off. . |
| WO 99/33457 | 7/1999 | WIPO . |
| WP 99/33456 | 7/1999 | WIPO . |

OTHER PUBLICATIONS

S.M. Walters, J. Pharm. Sci., 69, 1206 (1980).
Laizure et al., Ther. Drug. Mon. 7, 447 (1985).

*Primary Examiner*—James M. Spear
*Attorney, Agent, or Firm*—Thorpe North & Western LLP

[57] ABSTRACT

The present invention pertains to a stabilized pharmaceutical composition which comprises a mixture of (a) a pharmaceutical agent unstable at a pH above about 3.5; and (b) a stabilizing amount of an acidic pharmaceutically acceptable carrier to stabilize the pharmaceutical agent. The acidic pharmaceutically acceptable carrier is a dried premixture of a pharmaceutically acceptable carrier and an aqueous solution of an acid. The stabilized pharmaceutical composition has a pH value of less than about 3.5, and when stored at a temperature of about 50° C. for about 4 weeks at about 27% relative humidity, retains at least about 80% of the pharmaceutical agent. This invention also pertains to sustained-release forms of the stabilized pharmaceutical compositions as well as to novel methods for preparing and using the stabilized pharmaceutical compositions and to stabilized pharmaceutical compositions made by the novel method.

12 Claims, No Drawings

STABILIZED PHARMACEUTICAL COMPOSITIONS

BACKGROUND OF THE INVENTION

1. Field of the Invention

The present invention pertains to a stabilized pharmaceutical composition which comprises a mixture of (a) a pharmaceutical agent unstable at a pH above about 3.5; and (b) a stabilizing amount of an acidic pharmaceutically acceptable carrier to stabilize the pharmaceutical agent. The acidic pharmaceutically acceptable carrier is a dried premixture of a pharmaceutically acceptable carrier and an aqueous solution of an acid. The stabilized pharmaceutical composition has a pH value of less than about 3.5, and when stored at a temperature of about 50° C. for about 4 weeks at about 27% relative humidity, retains at least about 80% of the pharmaceutical agent. This invention also pertains to both immediate release forms and sustained-release forms of the stabilized pharmaceutical compositions as well as to novel methods for preparing and using the stabilized pharmaceutical compositions and to stabilized pharmaceutical compositions made by the novel method.

2. Description of the Background

One of the requirements for an acceptable pharmaceutical composition is that it must be stable, so as not to exhibit substantial decomposition of the active ingredient during the time between manufacture of the composition and use by the patient. A number of drugs are known to undergo hydrolytic decomposition, which is one of the most common routes of drug decompositions. Further, hydrolytic decomposition can be influenced by light, oxidation, and pH. For example, diethylpropion hydrochloride is known to slowly hydrolytically decompose in aqueous solution at pH 3.5 and below, but rapidly decompose at pH 3.5 and above. Stephen M. Walters, "Influence of pH on Hydrolytic Decomposition of Diethylpropion Hydrochloride: Stability Studies on Drug Substance and Tablets Using High-Performance Liquid Chromatography", J. Pharm. Science 69, 1206 (1980). The hydrolytic decomposition of bupropion hydrochloride has also been shown to have similar pH dependence. S. Casey Laizure and C. Lindsay DeVane, "Stability of Bupropion and its Major Metabolite in Human Plasma", Therapeutic Drug Monitoring 7, 447 (1985).

U.S. Pat. No. 3,819,706 (Mehta) and U.S. Pat. No. 3,885,046 (Mehta) disclose the use of m-chloro-α-t-butylaminopropiophenone (bupropion) and m-fluoro-α-t-butylaminopropiophenone for the treatment of depression in mammals.

U.S. Pat. No. Re. 33,994 (Baker et al.) discloses a controlled release composition for the oral administration of bupropion hydrochloride. The composition releases about 10% to 45% of bupropion hydrochloride within two hours, about 25% to 70% of bupropion hydrochloride within four hours, and about 40% to 90% of bupropion hydrochloride within six hours.

U.S. Pat. No. 5,358,970 (Ruff et al.) discloses a solid pharmaceutical composition comprising bupropion hydrochloride and a pharmaceutically acceptable stabilizer. The stabilizer has an aqueous solution pH of about 0.9 to about 4 at an aqueous solution concentration of about 6% w/w. The composition, when stored for 4 weeks at about 50° C. and at about 27% relative humidity, contains at least about 80% of the labeled amount of bupropion hydrochloride in the composition. The stabilizer is selected from the group consisting of L-cysteine hydrochloride, glycine hydrochloride, malic acid, sodium metabisulfite, citric acid, tartaric acid, and L-cystine dihydrochloride.

U.S. Pat. No. 5,427,798 (Ludwig et al.) discloses a controlled sustained-release tablet comprising 25 to 500 mg of bupropion hydrochloride and hydroxypropyl methylcellulose. The amount of hydroxypropyl methylcellulose to one part of bupropion hydrochloride is 0.19 to 1.1. The tablet has a surface to volume ratio of 3:1 to 25:1 $cm^{-1}$ and a shelf life of at least one year at 59° F. to 77° F. The tablet releases between about 20 and 60% of bupropion hydrochloride in water in 1 hour, between about 50 and 90% in 4 hours, and not less than about 75% in 8 hours.

U.S. Pat. No. 4,743,450 (Harris et al.) discloses a pharmaceutical composition which contains a drug component which comprises a suitable amount of an ACE inhibitor which is susceptible to cyclization, hydrolysis, and discoloration; a suitable amount of an alkaline earth metal carbonate to inhibit cyclization and discoloration; and a suitable amount of a saccharide to inhibit hydrolysis.

U.S. Pat. No. 5,350,582 (Merslavic et al.) discloses a process for preparing stable formulation of enalapril sodium salt. The process includes suspending enalapril maleate in demineralized water and a stoichiometric amount of a corresponding sodium compound selected from the group consisting of sodium carbonate, sodium hydrogen carbonate and sodium hydroxide.

U.S. Pat. No. 5,292,520 (de Haan et al.) discloses an improved granulation process utilizing temperatures greater than 45° C. and involving a mixture of a water-soluble acid addition salt of a poorly soluble basic drug and an excipient. The process consists of selecting a drug from the group consisting of chloropromazine, imipramine, promethazine, and mianserin, selecting an excipient from the group consisting of microcrystalline cellulose, lactose, and calcium hydrogen phosphate, and adding a pharmaceutically acceptable alkaline compound having a water solubility of at least 2 mg/ml to the mixture before or during heating. The pharmaceutically acceptable alkaline compound is present in an amount from about 0.5% to about 10% by weight.

U.S. Pat. No. 5,441,747 (de Haan et al.) discloses a dry pharmaceutical preparation consisting essentially of a water-soluble acid addition salt of a poorly soluble basic drug selected from the group consisting of apomorphine, chlorpromazine, imipramine, promethazine, and mianserin; an excipient selected from the group consisting of microcrystalline cellulose, lactose, and calcium hydrogen phosphate in an amount from about 30 to about 80% by weight and a water-soluble alkaline stabilizer in an amount from about 0.5 to about 10% by weight preparation. The stabilizer is selected from the group consisting of sodium bicarbonate, ammonium carbonate, sodium citrate, dibasic sodium phosphate, anhydrous dibasic sodium biphosphate, diammonium hydrogen phosphate, and sodium pyrophosphate.

U.S. Pat. No. 5,562,921 (Sherman) discloses a stable solid pharmaceutical composition comprising enalapril maleate and a carrier. The carrier is substantially free of microcrystalline cellulose, cellulose derivatives or cellulose polymers and calcium phosphate and free or substantially free of a disintegrant. At least 50% of the carrier consists of one or more pharmaceutically acceptable water-soluble substances not being cellulose derivatives or cellulose polymers. The carrier is substantially free of magnesium stearate and includes a lubricant which is not magnesium stearate.

U.S. Pat. No. 5,573,780 (Sherman) discloses a process of manufacture of a pharmaceutical solid composition comprising enalapril sodium. The process comprises i) a) mixing enalapril maleate with an alkaline sodium compound and at least one other excipient, adding water sufficient to moisten, and mixing to achieve a wet mass; or b) mixing enalapril maleate with at least one excipient other than an alkaline sodium compound, adding a solution of an alkaline sodium compound in water sufficient to moisten and mixing to achieve a wet mass thereby to achieve a reaction without converting the enalapril maleate to a clear solution of enalapril sodium and maleic acid sodium salt in water; ii) drying the wet mass; and iii) further processing the dried material into tablets.

European patent application no. 0 380 021 (Abbott) discloses an improved pharmaceutical preparation using tromethemine and dibasic potassium phosphate or calcium carbonate to enhance stability.

U.S. Pat. No. 4,591,592 (Chowhan) discloses a stable pharmaceutical composition comprising a therapeutically effective amount of an active ingredient which is a pharmaceutically acceptable acid addition salt of a thieno-pyridine derived compound and a non-toxic stabilizing amount of a pharmaceutically, non-volatile acidic compound which is ascorbic acid, benzoic acid, citric acid, fumaric acid, or tartaric acid, and at least one pharmaceutically acceptable excipient.

U.S. Pat. No. 5,225,204 (Chen et al.) discloses a stabilized pharmaceutical formulation of Levothyroxine sodium comprising a complex of Levothyroxine sodium and a water-soluble polyvinylpyrrolidone adsorbed on a cellulose compound in the form of a tablet.

SUMMARY OF THE INVENTION

The present invention pertains to a stabilized pharmaceutical composition which comprises a mixture of:
(a) a pharmaceutical agent unstable at a pH above about 3.5; and
(b) a stabilizing amount of an acidic pharmaceutically acceptable carrier to stabilize the pharmaceutical agent, wherein the acidic pharmaceutically acceptable carrier is a dried premixture of a pharmaceutically acceptable carrier and an aqueous solution of an acid;
wherein the stabilized pharmaceutical composition has a pH value of less than about 3.5, and when stored at a temperature of about 50° C. for about 4 weeks at about 27% relative humidity, retains at least about 80% of the pharmaceutical agent.

The present invention also pertains to a method for stabilizing a pharmaceutical composition which comprises the step of:
(a) premixing a pharmaceutically acceptable carrier and an aqueous solution of an acid;
(b) drying the premixture from step (a) to form an acidic pharmaceutically acceptable carrier; and
(c) admixing a stabilizing amount of the dried acidic pharmaceutically acceptable carrier from step (b) with a pharmaceutical agent unstable at a pH above about 3.5 to form a stabilized pharmaceutical composition;
wherein the stabilized pharmaceutical composition has a pH value of less than about 3.5, and when stored at a temperature of about 50° C. for about 4 weeks at about 27% relative humidity, retains at least about 80% of the pharmaceutical agent.

The present invention further pertains to a stabilized pharmaceutical composition prepared by a method which comprises the step of:
(a) premixing a pharmaceutically acceptable carrier and an aqueous solution of an acid;
(b) drying the premixture from step (a) to form an acidic pharmaceutically acceptable carrier; and
(c) admixing a stabilizing amount of the dried acidic pharmaceutically acceptable carrier from step (b) with a pharmaceutical agent unstable at a pH above about 3.5 to form a stabilized pharmaceutical composition;
wherein the stabilized pharmaceutical composition has a pH value of less than about 3.5, and when stored at a temperature of about 50° C. for about 4 weeks at about 27% relative humidity, retains at least about 80% of the pharmaceutical agent.

The present invention further pertains to a sustained-release stabilized pharmaceutical composition which comprises a mixture of:
(A) a premixture of a stabilized pharmaceutical composition comprising:
(a) a pharmaceutical agent unstable at a pH above about 3.5; and
(b) a stabilizing amount of an acidic pharmaceutically acceptable carrier to stabilize the pharmaceutical agent, wherein the acidic pharmaceutically acceptable carrier is a dried premixture of a pharmaceutically acceptable carrier and an aqueous solution of an acid;
wherein the stabilized pharmaceutical composition has a pH value of less than about 3.5, and when stored at a temperature of about 50° C. for about 4 weeks at about 27% relative humidity, retains at least about 80% of the pharmaceutical agent; and
(B) from about 1% to about 70%, by weight, of a hydrophilic polymer or a wex matrix polymer.

DETAILED DESCRIPTION OF THE INVENTION

The present invention is directed to an improved stabilized pharmaceutical composition for stabilizing pharmaceutical agents unstable at a pH above about 3.5. Applicants have discovered that stabilized pharmaceutical compositions can be prepared by premixing a pharmaceutically acceptable carrier and an aqueous solution of an acid, drying the premixture to form an acidic pharmaceutically acceptable carrier, and admixing the dried acidic pharmaceutically acceptable carrier with the otherwise unstable pharmaceutical agent to form a stabilized pharmaceutical composition. Other commonly used excipients may also be admixed into the stabilized pharmaceutical composition at this point. When the premixture of pharmaceutically acceptable carrier and aqueous solution of an acid is dried, the pharmaceutically acceptable carrier appears to become coated with, or otherwise bound to, the concentrated acid thereby creating an acidic stabilizing microenvironment around the otherwise unstable pharmaceutical agent. The stabilized pharmaceutical compositions of the present invention are surprisingly stable, have satisfactory shelf lives, and meet current compendial and regulatory potency and decomposition requirements. The stabilized pharmaceutical compositions exhibit both immediate and sustained-release drug release. This invention also pertains to sustained-release forms of the stabilized pharmaceutical compositions as well as to novel methods for preparing and using the stabilized pharmaceutical compositions and to stabilized pharmaceutical compositions made by the novel method.

In accord with the present invention, a stabilized pharmaceutical composition is provided which comprises a mixture of: (a) a pharmaceutical agent unstable at a pH above about 3.5; and (b) a stabilizing amount of an acidic pharmaceutically acceptable carrier to stabilize the pharmaceutical agent. The acidic pharmaceutically acceptable carrier is a dried premixture of a pharmaceutically acceptable carrier and an aqueous solution of an acid. The stabilized pharmaceutical composition has a pH value of less than about 3.5. When stored at a temperature of about 50° C. for about 4 weeks at about 27% relative humidity, the stabilized pharmaceutical composition retains at least about 80% of the pharmaceutical agent.

The pharmaceutical agent in the present invention is a drug which is unstable in aqueous solution at a pH above about 3.5. Preferably, the pharmaceutical agent is unstable in aqueous solution at a pH above about 4.5, more preferably, at a pH above about 5.5, and most preferably, at a pH above about 6.5. As used herein, the term "pharmaceutical agent that is unstable in aqueous solution at a pH above about 3.5" refers to an agent that, when stored in aqueous solution at a pH above about 3.5 at about 45° C. for about 40 days, retains less than about 90% of the pharmaceutical agent. Preferably, the pharmaceutical agent unstable in aqueous solution at a pH above about 3.5, when stored in aqueous solution at a pH above about 3.5 at about 45° C. for about 40 days, retains less than about 80% of the pharmaceutical agent, more preferably, the pharmaceutical agent retains less than about 90% of the pharmaceutical agent, and most preferably, the pharmaceutical agent retains less than about 95% of the pharmaceutical agent.

The pharmaceutical agent in the present invention may be selected from a wide variety of drugs which are unstable in aqueous solution at a pH above about 3.5. Illustrative examples of classes of compounds unstable at a pH above about 3.5 include α-aminopropiophenones and thienopyidine derived compounds. Illustrative examples of specific types of α-aminopropiophenones include bupropion (m-chloro-α-t-butylaminopropiophenone), m-fluoro-α-t-butylaminopropiophenone, and diethylpropion hydrochloride. Illustrative examples of specific types of thienopyidine derived compounds include ticlopidine hydrochloride. In a preferred embodiment, the pharmaceutical agent is selected from the group consisting of bupropion hydrochloride and diethylpropion hydrochloride. In a more preferred embodiment, the pharmaceutical agent unstable in aqueous solution at a pH above about 3.5 is bupropion hydrochloride (1-(3-chlorophenyl)-2-[(1,1-dimethylethyl)amino]-1-propanone, 2-(tert-butylamino)-3'-chloropropiophenone).

Bupropion hydrochloride ((+)-2-(tert-butylamino)-3'-chloropropiophenone hydrochloride) is an antidepressant marketed in both immediate release forms and sustained-release forms. Bupropion hydrochloride is available in 75 mg and 100 mg immediate release tablets and 100 mg and 150 mg sustained-release tablets. Drug loading of bupropion hydrochloride may be from about 1% to about 70%, and preferably from about 10% to about 40%. Bupropion hydrochloride is normally expressed chemically as $C_{13}H_{18}ClNO \cdot HCl$. Bupropion hydrochloride is very stable in a solid-state by itself, however, in combination with commonly used pharmaceutical carrier(s), bupropion hydrochloride is highly unstable as evident by rapid decay in its potency and development of characteristic odor.

The amount of pharmaceutical agent present in the stabilized pharmaceutical compositions of the present invention is a therapeutically effective amount. A therapeutically effective amount of a pharmaceutical agent is that amount of agent necessary to exert its intended therapeutic effect. The exact amount of pharmaceutical agent may be a matter of preference subject to such factors as the type of condition being treated as well as the other ingredients in the composition. The exact amount of pharmaceutical agent is well known to those of skill in the art and is not the subject of this invention.

As set out above, the acidic pharmaceutically acceptable carrier is a dried premixture of a pharmaceutically acceptable carrier and an aqueous solution of an acid. The pharmaceutically acceptable carrier in the present invention may be any pharmaceutically acceptable carrier which may be coated with, or otherwise bound to, an aqueous solution of an acid to form an acidic microenvironment around the pharmaceutically acceptable carrier thereby stabilizing the pharmaceutical agent. Specifically, the pharmaceutically acceptable carrier must be able to form a stabilized pharmaceutical composition having a pH value of less than about 3.5. The pharmaceutically acceptable carrier must also be stable to the aqueous solution of acid employed during the premixture step. Illustrative examples of pharmaceutically acceptable carriers include microcrystalline cellulose (MCC), powdered cellulose, lactose, and starch. Preferably, the pharmaceutically acceptable carrier is microcrystalline cellulose or powdered cellulose. More preferably, the pharmaceutically acceptable carrier is microcrystalline cellulose.

Microcrystalline cellulose is a purified, partially depolymerized cellulose prepared by treating alpha-cellulose, obtained as a pulp from fibrous plant material. Microcrystalline cellulose NF is available, for example, from FMC Corporation under the trade name Avicel® PH 101/102/103/105/200, in different average particles. Microcrystalline cellulose NF is also available from Mandell Corporation under the trade name EMCOCEL®.

The aqueous solution of acid in the pharmaceutically acceptable carrier premixture may be any pharmaceutically acceptable aqueous solution of acid which will coat, or otherwise be bound to, a pharmaceutically acceptable carrier to form an acidic microenvironment around the pharmaceutically acceptable carrier thereby stabilizing the pharmaceutical agent. Specifically, the aqueous solution of an acid must be able to form a stabilized pharmaceutical composition with the pharmaceutically acceptable carrier having a pH value of less than about 3.5. The aqueous solution of acid must also not degrade the pharmaceutically acceptable carrier employed during the premixture step. Illustrative examples of aqueous solutions of acid for premixing with the pharmaceutically acceptable carrier include hydrochloric acid, nitric acid, sulfuric acid, and phosphoric acid. The more preferred acid for premixing with the pharmaceutically acceptable carrier is hydrochloric acid. Hydrochloric acid is the preferred acid because it is found in the mammalian gastrointestinal tract.

In a preferred embodiment, the acidic pharmaceutically acceptable carrier is a dried premixture of microcrystalline cellulose and hydrochloric acid. The dried acidic pharmaceutically acceptable carrier may be purchased directly from the manufacturer of the pharmaceutically acceptable carrier or may be made by premixing the pharmaceutically acceptable carrier with the aqueous solution of acid prior to introducing the pharmaceutical agent.

The amount of acidic pharmaceutically acceptable carrier present in the stabilized pharmaceutical compositions of the present invention is a stabilizing amount to stabilize the pharmaceutical agent. A stabilizing amount of acidic pharmaceutically acceptable carrier is that amount of acidic pharmaceutically acceptable carrier necessary to stabilize the otherwise unstable pharmaceutical agent. The exact amount of acidic pharmaceutically acceptable carrier is a matter of preference subject to such factors as the type and amount of pharmaceutical agent being stabilized as well as the type of pharmaceutically acceptable carrier and aqueous solution of acid employed along with the other ingredients in the composition. The stabilized pharmaceutical composition, when prepared in accord with the present invention, has a pH value of less than about 3.5. Preferably, the stabilized pharmaceutical composition has a pH value from about 2.5 to about 3.5. More preferably, the stabilized pharmaceutical composition has a pH value from about 2.7 to about 3.3. In a preferred embodiment, the acidic pharmaceutically acceptable carrier is present in the stabilized pharmaceutical composition in an amount from about 1% to about 80%, preferably from about 5% to about 75%, and more preferably from about 10% to about 75%, by weight of the stabilized pharmaceutical composition.

When prepared in accord with the present invention, the stabilized pharmaceutical composition, when stored at a temperature of about 50° C. for about 4 weeks at about 27% relative humidity, retains at least about 80% of the pharmaceutical agent. More preferably, the stabilized pharmaceutical composition retains at least about 90% of the pharmaceutical agent. Most preferably, the stabilized pharmaceutical composition retains at least about 95% of the pharmaceutical agent.

Many compositions containing bupropion hydrochloride were produced and tested for stability. Stability testing was carried out by the technique known as stress stability (about 50° C. for about 2–4 weeks) and/or as accelerated stability (40° C.-75% RH for about 6 months). In such studies, samples are stored at elevated temperatures. This speeds decomposition and shortens the time needed to draw conclusions on stabilized compositions. At a temperature of about 50° C., for example, decomposition that would take months at ambient temperature will occur within a few weeks. At the end of the desired test period, samples are removed from the stability chambers and tested for extent of decomposition. The measurements of decomposition and potency were done using high performance liquid chromatographic (HPLC) method.

The pH values of the stabilized pharmaceutical test compositions were measured by weighing approximately 3 grams of the test composition and dispersing the test composition in 50 mL of water. The dispersion is stirred. Stirring is stopped and the pH is measured.

In a specific embodiment, the stabilized pharmaceutical composition is an immediate release tablet comprising bupropion hydrochloride. The bupropion hydrochloride 75 mg and 100 mg immediate release tablets of the present invention comprise:

| Core Ingredients | % w/w | 75 mg/tablet | 100 mg/tablet |
| --- | --- | --- | --- |
| Bupropion hydrochloride | 16.7 | 75 | 100 |
| MCC premix* | 73.3 | 330 | 440 |
| Talc | 10.0 | 45 | 60 |
| Total | 100 | 450 | 600 |
| Coating Ingredients Opadry ™ Pink solids | | 6–8 | 36–48 |

*Microcrystalline Cellulose premix wet granulated with dilute hydrochloric acid and dried.
The pH of the final product is approximately 3.0.

The pH of the final product is approximately 3.0.

The present invention extends to methods for making the stabilized pharmaceutical compositions. In general, the method for making the stabilized pharmaceutical composition may be illustrated by a method for manufacturing bupropion hydrochloride immediate release tablets which involves the steps of: granulating microcrystalline cellulose with hydrochloric acid followed by drying and milling; mixing the bupropion hydrochloride with milled microcrystalline cellulose and talc; compressing the mixture to form tablet cores; and coating the core tablets with Opadry solids. The pH of the hydrochloric acid at 6% w/w aqueous solution is approximately zero. Every 100 mg of microcrystalline cellulose contains 0.4 mg of hydrochloric acid. The bupropion hydrochloride immediate release tablets will release about 80% of the drug into dissolution media within 30 minutes.

In a specific embodiment, the present invention is directed to a method for stabilizing a pharmaceutical composition which comprises the step of:
  (a) premixing a pharmaceutically acceptable carrier and an aqueous solution of an acid;
  (b) drying the premixture from step (a) to form an acidic pharmaceutically acceptable carrier; and
  (c) admixing a stabilizing amount of the dried acidic pharmaceutically acceptable carrier from step (b) with a pharmaceutical agent unstable at a pH above about 3.5 to form a stabilized pharmaceutical composition;
wherein the stabilized pharmaceutical composition has a pH value of less than about 3.5, and when stored at a temperature of about 50° C. for about 4 weeks at about 27% relative humidity, retains at least about 80% of the pharmaceutical agent.

In another specific embodiment, the present invention is directed to a stabilized pharmaceutical composition prepared by a method which comprises the step of:
  (a) premixing a pharmaceutically acceptable carrier and an aqueous solution of an acid;
  (b) drying the premixture from step (a) to form an acidic pharmaceutically acceptable carrier; and
  (c) admixing a stabilizing amount of the dried acidic pharmaceutically acceptable carrier from step (b) with a pharmaceutical agent unstable at a pH above about 3.5 to form a stabilized pharmaceutical composition;
wherein the stabilized pharmaceutical composition has a pH value of less than about 3.5, and when stored at a temperature of about 50° C. for about 4 weeks at about 27% relative humidity, retains at least about 80% of the pharmaceutical agent.

A variety of traditional ingredients which do not interfere with the function of the acidic pharmaceutically acceptable carrier may optionally be included in the stabilized pharmaceutical composition in effective amounts. Generally, lubricants such as talc, hydrogenated vegetable oil, stearic acid; binders, such as polyvinylpyrrolidone, gelatin; and/or disintegrant, such as polyplasdone, are suitable. Other optional ingredients include buffers, preservatives, tonicity adjusting agents, antioxidants, polymers for adjusting viscosity or for use as extenders, and excipients, and the like. Other conventional additives include humectants, emollients, lubricants, stabilizers, dyes, providing the additives do not interfere with the therapeutic properties of the stabilized pharmaceutical composition. Other conventional pharmaceutical additives known to those having ordinary skill in the pharmaceutical arts may also be used in the pharmaceutical composition. The ultimate pharmaceutical compositions are readily prepared using methods generally known in the pharmaceutical arts.

In another embodiment, the present invention is directed to a sustained-release stabilized pharmaceutical composition which comprises a mixture of:
  (A) a premixture of a stabilized pharmaceutical composition comprising:
    (a) a pharmaceutical agent unstable at a pH above about 3.5; and (b) a stabilizing amount of an acidic pharmaceutically acceptable carrier to stabilize the pharmaceutical agent, wherein the acidic pharmaceutically acceptable carrier is a dried premixture of a pharmaceutically acceptable carrier and an aqueous solution of an acid;

wherein the stabilized pharmaceutical composition has a pH value of less than about 3.5, and when stored at a temperature of about 50° C. for about 4 weeks at about 27% relative humidity, retains at least about 80% of the pharmaceutical agent; and (B) from about 1% to about 70%, by weight, of a hydrophilic polymer or a wex matrix polymer.

The hydrophilic polymers which may be employed in the sustained-release stabilized pharmaceutical compositions of the present invention may be selected from the group consisting of hydrophilic polymers or wax matrix polymers. Suitable hydrophilic polymers include carboxypolymethylene polymers and poly(ethylene oxide). Carboxypolymethylene polymers (carbomer, Carbopol®, carboxyvinyl polymer) are water-soluble, highly ionic, slightly acidic, vinyl polymers with active carboxyl groups. Poly(ethylene oxide) polymers (PEO) are water-soluble, non-ionic, polyether homopolymers having molecular weights from about 100,000 to about 5,000,000. Suitable wax matrix polymers include polyvinyl alcohol, hydroxypropyl cellulose, cetyl alcohol, carnauba wax, stearyl alcohol, gums, hydrocolloids, including xanthan gums, guar gums, and carrageenan gums.

The hydrophilic polymer may be present in the sustained-release stabilized pharmaceutical composition in an amount from about 1% to about 70%, preferably from about 5% to about 40%, and more preferably from about 10% to about 30%, by weight.

The present invention is further illustrated by the following examples which are not intended to limit the effective scope of the claims. All parts and percentages in the examples and throughout the specification and claims are by weight of the final composition unless otherwise specified.

EXAMPLES

Example A

Preparation of a Stabilized Pharmaceutical Composition

This example illustrates a method for preparing a stabilized pharmaceutical composition in immediate release form in a preferred embodiment of the present invention.

| Ingredient(s) | Quantity |
| --- | --- |
| Bupropion HCl | 50.1 Kg/batch (16.7% w/w) |
| Microcrystalline Cellulose, NF [Avicel ® PH101] | 220.0 Kg/Batch (73.3% w/w) |
| Dilute Hydrochloric Acid, NF | 8.03 Kg/Batch* |
| Purified Water, USP | 102.0 Kg/Batch* |
| Talc, NF | 30.0 Kg/Batch (10.0% w/w) |

*removed during processing step, drying.

A dried acidic pharmaceutically acceptable carrier premixture comprising a pharmaceutically acceptable carrier and an aqueous solution of acid was prepared as follows. Dilute hydrochloric acid, NF was slowly added with gentle mixing to Purified Water, USP in a stainless steel kettle to form an aqueous hydrochloric acid solution, approximately 0.2N. Microcrystalline cellulose was passed through a #8 mesh screen using Sweco sifting device. The aqueous solution of hydrochloric acid was then added with slow mixing to the sieved microcrystalline cellulose. After the aqueous solution of hydrochloric acid was thoroughly mixed with the microcrystalline cellulose, the wet microcrystalline cellulose was then dried in a forced air oven (inlet air temperature of about 45–50° C.). The dried acidic microcrystalline cellulose was then milled in a Fitzmill using a 1531-0093 (#2A) screen (knives forward, high speed).

The milled acidic microcrystalline cellulose granulation premix and bupropion hydrochloride were then placed in a V-blender and blended thoroughly. Talc was then added to the V-blender and thoroughly blended into a the mix to prepare the final stabilized pharmaceutical composition. Preferably, the hydrochloric acid content in the milled acidic microcrystalline cellulose granulation premix is present in an amount of about 1.6% by weight of bupropion hydrochloride. The pH of the final composition was about 2.7–3.0.

Example B

The Effect of Moisture Content of Microcrystalline Cellulose

| Ingredient(s) | Quantity |
| --- | --- |
| Bupropion HCl | 16.7% w/w |
| Microcrystalline Cellulose, NF [Avicel ® PH102 or PH112] | 73.3% w/w |
| Talc, NF | 10.0 w/w |

Since the primary route of bupropion decomposition is hydrolytic, the composition in this example was designed to study the effect of the moisture content of microcrystalline cellulose (major carrier) on bupropion stability. Bupropion HCl was thoroughly mixed with either Avicel® PH102 grade of microcrystalline cellulose, NF (moisture content of about 3–4%) or Avicel® PH112 grade of microcrystalline cellulose, NF (moisture content of about 1–2%). After mixing, talc was added to the composition and thoroughly mixed. The pH of both compositions (one comprising PH102 and the other PH112) were observed to be about 5–5.5.

Example C

The Effect of Alginic Acid

| Ingredient(s) | Quantity |
| --- | --- |
| Bupropion HCl | 16.7% w/w |
| Microcrystalline Cellulose, NF [Avicel ® PH102] | 69.6% w/w |
| Alginic Acid, NF | 3.75% w/w |
| Purified Water, USP | (*) |
| Talc, NF | 10.0 w/w |

*removed during processing step, drying.

Alginic acid, NF is a pharmaceutically acceptable binder/disintegrant, which is acidic in nature. The pH of a 3% aqueous dispersion is about 1.5–3.5. Bupropion HCl and microcrystalline cellulose (Avicel® PH102) were mixed and wet granulated using aqueous solution of alginic acid in purified water. The wet mass was dried, milled and mixed with talc thoroughly in a V-blender. The pH of the composition is about 4.5–5.0.

Example D
The Effect of Colloidal Silica, a Moisture Scavenger

| Ingredient(s) | Quantity |
|---|---|
| Bupropion HCl | 16.7% w/w |
| Microcrystalline Cellulose, NF [Avicel ® PH112] | 78.3% w/w |
| Colloidal Silicone Dioxide, NF [Aerosil 200] | 5.0% w/w |

Direct blend comprising of bupropion HCl, low moisture grade microcrystalline cellulose (Avicel PH112) and colloidal silicone dioxide (Aerosil 200) was prepared by thoroughly mixing the components. The pH of a 4% aqueous dispersion of colloidal silicone dioxide is about 3.5–4.4. The pH of the composition described in example D is about 5–5.5.

Example E
The Effect of Lactose, Pregelatinized Starch, and Colloidal Silica

| Ingredient(s) | Quantity |
|---|---|
| Bupropion HCl | 16.7% w/w |
| Lactose Anhydrous, NF | 56.4% w/w |
| Pregelatinized Starch, NF [Starch 1500] | 22.0% w/w |
| Colloidal Silicone Dioxide, NF [Aerosil 200] | 3.3% w/w |
| Povidone, NF [Plasdone K-29/32] | 1.65% w/w |

This formulation was described in U.S. Pat. No. 3,885,046 (Mehta) and was prepared to compare this formulation with the stabilized pharmaceutical compositions of the present invention. Dry blending was used to prepare the final composition.

Example F
Stability Data

The stability data for the compositions of Examples A–E were determined either on stress stability or accelerated stability conditions and are set out below.

| | Storage Conditions | % Potency, Total Degradation Products |
|---|---|---|
| Example A | 3 months/ 40° C.-75% RH | 98.9%, None Detected |
| Example B: | 2 weeks/45° C. | |
| Avicel ® PH102 | | 52.4%, — |
| Avicel ® PH112 | | 72.3%, — |
| Example C | 2 weeks/50° C. | 89.3%, 5.17% |
| Example D | 2 weeks/50° C. | 89%, 15% |
| Example E | 2 weeks/50° C. | 94.4%, 5.3% |

In general, stability testing was carried out by the technique known as stress stability (about 50° C. for about 2–4 weeks) and/or as accelerated stability (40° C.-75% RH for about 6 months). In such studies, samples are stored at elevated temperatures. This speeds decomposition and shortens the time needed to draw conclusions on stabilized compositions. At a temperature of about 50° C., for example, decomposition that would take months at ambient temperature will occur within a few weeks. At the end of the desired test period, samples are removed from the stability chambers and tested for extent of decomposition. The measurements of decomposition and potency were done using high performance liquid chromatographic (HPLC) method.

As set out above, the potency of the composition of Example A (microcrystalline cellulose premixed with hydrochloric acid, pH of the final composition about 2.7–3.0.) was very high (98.9%) after storage for 3 months at 40° C. and no degradation products were detected. The potency of the composition of Example B (Avicel® PH102 grade of microcrystalline cellulose, NF (moisture content of about 3–4%) and Avicel® PH112 grade of microcrystalline cellulose, NF (moisture content of about 1–2%, pH of both compositions about 5–5.5), not premixed with hydrochloric acid) was very low after storage for 2 weeks at 45° C. The potency of the composition of Example C (microcrystalline cellulose and aqueous solution of alginic acid, pH of the composition about 4.5–5.0.) was low after storage for 2 weeks at 50° C. The potency of the composition of Example D (low moisture grade microcrystalline cellulose and colloidal silicone dioxide, pH of the composition about 5–5.5) was low after storage for 2 weeks at 50° C. The potency of the composition of Example E (Lactose, Pregelatinized Starch, and Colloidal Silica) was less than 95% after storage for 2 weeks at 50° C. These examples illustrate that the unstable pharmaceutical agents of the present invention can be stabilized in pharmaceutical compositions having a pH value of less than about 3.5.

Throughout this application, various publications have been referenced. The disclosures in these publications are incorporated herein by reference in order to more fully describe the state of the art.

Throughout this disclosure, applicants will suggest various theories or mechanisms by which applicant believes the components in the compositions function together to provide stabilized pharmaceutical compositions. While applicants may offer various mechanisms to explain the present invention, applicant does not wish to be bound by theory. These theories are suggested to better understand the present invention but are not intended to limit the effective scope of the claims.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

We claim:

1. A method for stabilizing a pharmaceutical composition which comprises the step of:
   a) premixing a pharmaceutically acceptable carrier and an aqueous solution of an acid;
   b) drying the premixture from step a) to form an acidic pharmaceutically acceptable carrier; and
   c) admixing a stabilizing amount of the dried acidic pharmaceutically acceptable carrier from step b) with a pharmaceutical agent unstable at a pH above about 3.5 to form a stabilized pharmaceutical composition, wherein
the acidic pharmaceutically acceptable carrier provides an acidic stabilizing microenvironment around the pharmaceutical agent.

2. The method for stabilizing a pharmaceutical composition according to claim 1, wherein the stabilized pharmaceutical composition has a pH value of less than about 3.5, and when stored at a temperature of about 50° C. for about 4 weeks at about 27% relative humidity, retains at least about 80% of the pharmaceutical agent.

3. The method according to claim 2, wherein the pharmaceutical agent is unstable at a pH above about 4.5.

4. The method according to claim 2, wherein the pharmaceutical agent, when stored in aqueous solution at a pH above about 3.5 at about 45° C. for about 40 days, retains less than about 90% of the pharmaceutical agent.

5. The method according to claim 2, wherein the pharmaceutical agent is selected from the group consisting of bupropion hydrochloride, diethylpropion hydrochloride, and ticlopidine hydrochloride.

6. The method according to claim 5, wherein the pharmaceutical agent is bupropion hydrochloride.

7. The method according to claim 2, wherein the pharmaceutically acceptable carrier is selected from the group consisting of microcrystalline cellulose, powdered cellulose, lactose, and starch.

8. The method according to claim 2, wherein the aqueous solution of an acid is selected from the group consisting of hydrochloric acid, nitric acid, sulfuric acid, and phosphoric acid.

9. The method according to claim 2, wherein the acidic pharmaceutically acceptable carrier is a dried premixture of microcrystalline cellulose and hydrochloric acid.

10. The method according to claim 2, wherein the stabilized pharmaceutical composition has a pH value from about 2.5 to about 3.5.

11. The method according to claim 2, wherein the stabilized pharmaceutical composition, when stored at a temperature of about 50° C. for about 4 weeks at about 27% relative humidity, retains at least about 90% of the pharmaceutical agent.

12. A stabilized pharmaceutical composition prepared by a method which comprises the step of:

(a) premixing a pharmaceutically acceptable carrier and an aqueous solution of an acid;

(b) drying the premixture from step (a) to form an acidic pharmaceutically acceptable carrier; and (c) admixing a stabilizing amount of the dried acidic pharmaceutically acceptable carrier from step (b) with a pharmaceutical agent unstable at a pH above about 3.5 to form a stabilized pharmaceutical composition;

wherein the stabilized pharmaceutical composition has a pH value of less than about 3.5, and when stored at a temperature of about 50° C. for about 4 weeks at about 27% relative humidity, retains at least about 80% of the pharmaceutical agent.

* * * * *